United States Patent [19]

Schaldach

[11] Patent Number: 5,215,084

[45] Date of Patent: Jun. 1, 1993

[54] CARDIAC PACEMAKER WITH ACTIVITY SENSOR

[75] Inventor: Max Schaldach, Erlangen, Fed. Rep. of Germany

[73] Assignee: Biotronik, Berlin, Fed. Rep. of Germany

[21] Appl. No.: 671,900

[22] PCT Filed: Jul. 16, 1990

[86] PCT No.: PCT/DE90/00543
§ 371 Date: Mar. 15, 1991
§ 102(e) Date: Mar. 15, 1991

[87] PCT Pub. No.: WO91/01157
PCT Pub. Date: Feb. 7, 1991

[30] Foreign Application Priority Data

Jul. 15, 1989 [DE] Fed. Rep. of Germany ....... 3923801

[51] Int. Cl.$^5$ ............................................. A61N 1/365
[52] U.S. Cl. .................................................. 128/419 PG
[58] Field of Search ................................. 128/419 PG

[56] References Cited

U.S. PATENT DOCUMENTS

| | | | |
|---|---|---|---|
| 4,140,132 | 2/1979 | Dahl | 128/419 PG |
| 4,428,378 | 1/1984 | Anderson et al. | 128/419 PG |
| 4,566,456 | 2/1986 | Koning et al. | 128/419 PG |
| 4,892,100 | 1/1990 | Schaldach | 128/419 PG |
| 4,919,137 | 4/1990 | Schaldach | 128/419 PG |
| 4,966,146 | 10/1990 | Webb et al. | 128/419 PG |
| 5,040,534 | 8/1991 | Mann et al. | 128/419 PG |

FOREIGN PATENT DOCUMENTS 0178528 4/1986 European Pat. Off. .
0331309 9/1989 European Pat. Off. .

Primary Examiner—William E. Kamm
Attorney, Agent, or Firm—Spencer, Frank & Schneider

[57] ABSTRACT

A cardiac pacemaker includes an activity sensor for detecting physical activity of a patient and generating a momentary output signal and an activity clock cycle generator having an adjustable clock cycle rate adjustable to the activity of the patient, for generating stimulation impulses for cardiac muscles of the patient at a rate defined by an end of one of a basic rate interval and an escape interval, the basic rate interval being a normal interval between stimulating impulses, and the escape interval being an on-demand interval between stimulating impulses. Varying circuitry for varying the basic rate interval and escape interval of the activity clock cycle generator between upper and lower fixed limits dependent on the activity of the patient detected by the activity sensor is provided, wherein the varying circuitry includes evaluation circuitry for generating a control signal for controlling the activity clock cycle generator as a time measurement for the rate of the stimulation impulses based on a comparison of the momentary output of the activity sensor with a threshold value. The rate of the stimulation impulses is thereby determined by the evaluation circuitry based on a relationship between a time the momentary output signal of the activity sensor remains above the threshold value and a time the momentary output signal of the activity sensor remains below the threshold value.

11 Claims, 3 Drawing Sheets

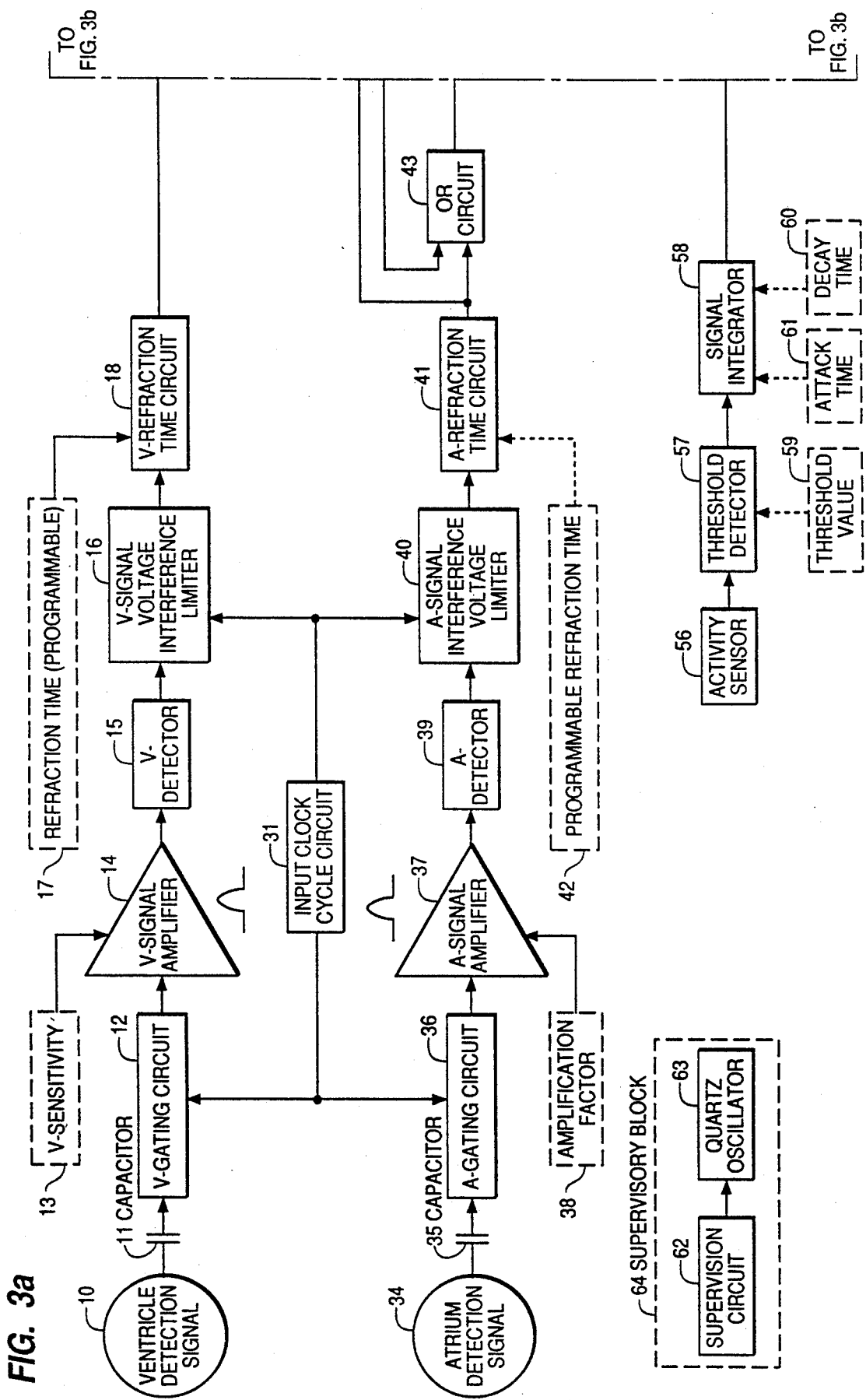

CARDIAC PACEMAKER WITH ACTIVITY SENSOR

BACKGROUND OF THE INVENTION

The invention relates to a physiologically operational, rate-adaptive cardiac pacemaker.

Such cardiac pacemakers are for example known from U.S. Pat. No. 4,140,132 and European Patent Application No. 0 080 348. The described cardiac pacemaker comprises an activity sensor which detects the intensity of movement of the patient. An evaluation circuit measures the output signal of a bending vibrator and evaluates the spectral peaks which are created by an activity of the patient above a defined programmable predeterminable threshold. The basic pacing rate of the cardiac pacemaker is varied in accordance with these detected activity levels which change together with each activity of the patient and—in the case of a demand pacemaker—the escape sequences of the pacemaker are also varied between the predetermined minimum and maximum values.

The known cardiac pacemakers have the disadvantage that the rate of change of the stimulation rate is only dependent on the number of the signals received which characterize the activity of the patient and do not provide any information about the signal intensity. For example, when the patient moves by walking, only the step speed 'ut not the step intensity can be measured, so that the difference between an exhausting jog with a larger step length and a walk at the same step speed but with a smaller step length cannot be determined.

SUMMARY OF THE INVENTION

The object of this invention is to provide an implantable cardiac pacemaker which can evaluate a basic stimulation rate (an escape sequence in the case of demand stimulation) from the output signal of a bending vibrator which is closely related to the actual physiological needs of the patient.

This object is achieved by the characteristics set out in claim 1. Advantageous features of the invention are set out in the dependent claims.

The invention is based on the realization that an evaluation of the amplitude values of the impulse signals created by the bending vibrator above the programmed threshold contains additional information concerning the actual cardiac output requirements of the patient. That means that the output signal, which is derived from the activity signals which are representative for the activity of the patient, is dependent on the amplitude of the impulses above the programmably set threshold. The escape sequence, which is derived from the output signal, is therefore always closely related to the actual physiological needs of the patient.

With the cardiac pacemaker according to the invention, control signals for the stimulation impulses are generated by an evaluation circuit in accordance with the detected patient activity, whereby these stimulation impulses are detected from a weighted time-mean of the relationship between the time a bandwidth-limited momentary sensor output signal remains above and below the threshold value.

In contrast to the band limiting described in EP-A-0 080 348, in which only frequency ranges between 10 and 100 Hz can pass through, a preferred embodiment of the cardiac pacemaker according to the invention uses a band pass filter, which lets those output signals of the sensor through, which are created by the movement of the patient and which lie, in particular, in the frequency range between 2 and 8 Hz.

The weighting factors of the cardiac pacemaker according to the invention, with which the filtered output impulses of the sensor are weighted, are different for the momentary signal levels above and below the predetermined threshold. They are chosen in such a manner that the impulses which are meaned in a later stage form a control signal which lead to a relatively steep-sloped increase of the basic stimulation rate if they exceed the threshold value and which lead, on average, to a flat-sloped decrease of the basic stimulation rate if they fall below the threshold value—whereby the weighting factors are chosen to correspond with the natural physiological conditions in accordance with the increasing cardiac activity due to a bodily load or in accordance with the decreasing cardiac activity if the workload is removed as detected in the related activitiy signals.

The weighting factors can be programmably altered in accordance with an advantageous feature of the invention and correspond therefore in this way with the programmed numerical values for the attack and decay times (related in each case to predetermined cardiac pacing differences).

The stimulation pacing control is dependent on the mean amplitude value of the oscillations within the time above the threshold if the signal magnitude increases with the output amplitude of the sensor during the time above the threshold.

BRIEF DESCRIPTION OF THE DRAWINGS

A preferred embodiment of the invention will be described below together with the drawings. They show.

DESCRIPTION OF THE PREFERRED EMBODIMENTS

Figure 1:
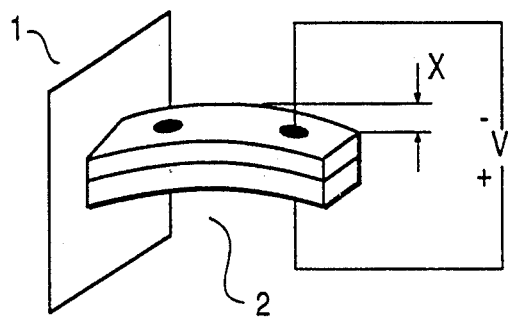
FIG. 1—a preferred embodiment of a bending vibrator used as a sensor in a cardiac pacemaker according to the invention.

FIG. 1 shows a bending vibrator 2, which is located inside the cardiac pacemaker housing 1. Such a bending vibrator 2 can be a piezo-ceramic strip whose deflection x, which is caused by the sound pressure wave of the activity of the patient is converted into corresponding voltage amplitudes by a convertor. The bending vibrator 2, due to its frequency characteristic, acts as the high-pass edge of the band limitation of the input signal. The low-pass edge is formed by a succeeding input filter which is realized by way of a differential amplifier. The thus formed band-pass filter has a ranging from 2 to 8 Hz with a quality-factor $Q=0.707$.

Figure 2A:
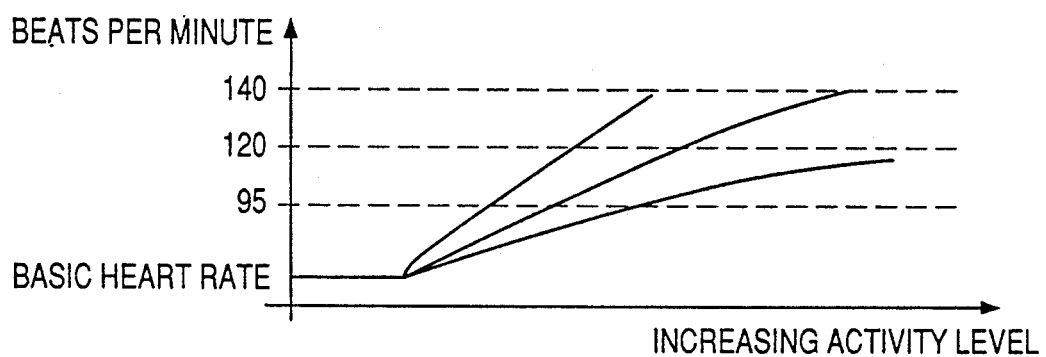
FIG. 2a—the programmable alterable pacing behaviour of the cardiac pacemaker with increasing activity.
Figure 2B:
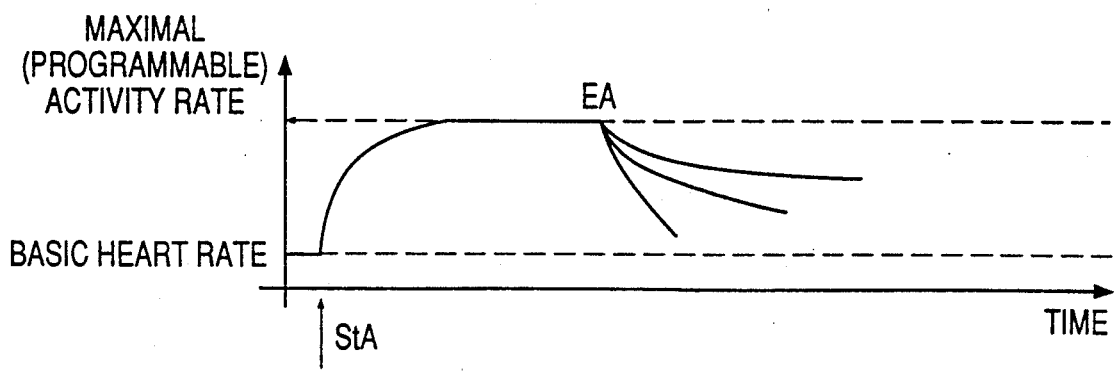
FIG. 2b—the programmable alterable pacing behaviour of the cardiac pacemaker with decreasing activity and FIGS. 3a and 3b—a block circuit diagramm of the signal processing circuit.

FIGS. 2a and 2b show the pacing control behaviour and its dependence on the activity of the patient whereby it strictly speaking is an open-loop control due to the missing feedback. According to the invention, two different control parameter characteristic curves are used with three programmable staring values each. FIG. 2a shows the control parameter characteristic curves for the time of increasing patient activity (attack time) and FIG. 2b the control parameter characteristic curves for the time of decreasing patient activity (decay time). In accordance with the patients requirements the basic heart beat can be BR 62, 72, or 82 beats per minute PPM (FIG. 2a) and the maximal programmable activity rate MAR can be 100, 125 or 150 beats per minute. The created impulse pacing rate is linearly dependent on the beat pacing rate control voltage which is a function of the chosen control parameter characteristic curve. The increasing activity level is plotted along the abscissa in FIG. 2a and time is plotted along the abscissa in FIG. 2b. If the voltage of the sensor is greater than the threshold voltage, the beat pacing rate control voltage increases to a value which is evaluated from the predetermined attack time, whereby this programmable time of increasing activity can have a value of 2, 4 or 8 seconds. If the sensor voltage is smaller than the threshold voltage, the beat pacing control voltage decreases by a value which has been evaluated using the predetermined decay time, whereby this programmable time of decreasing activity can have a value of 30, 50 or 100 seconds and is related to the return to the basic heart rate when physical activity ceases.

Figure 3B:
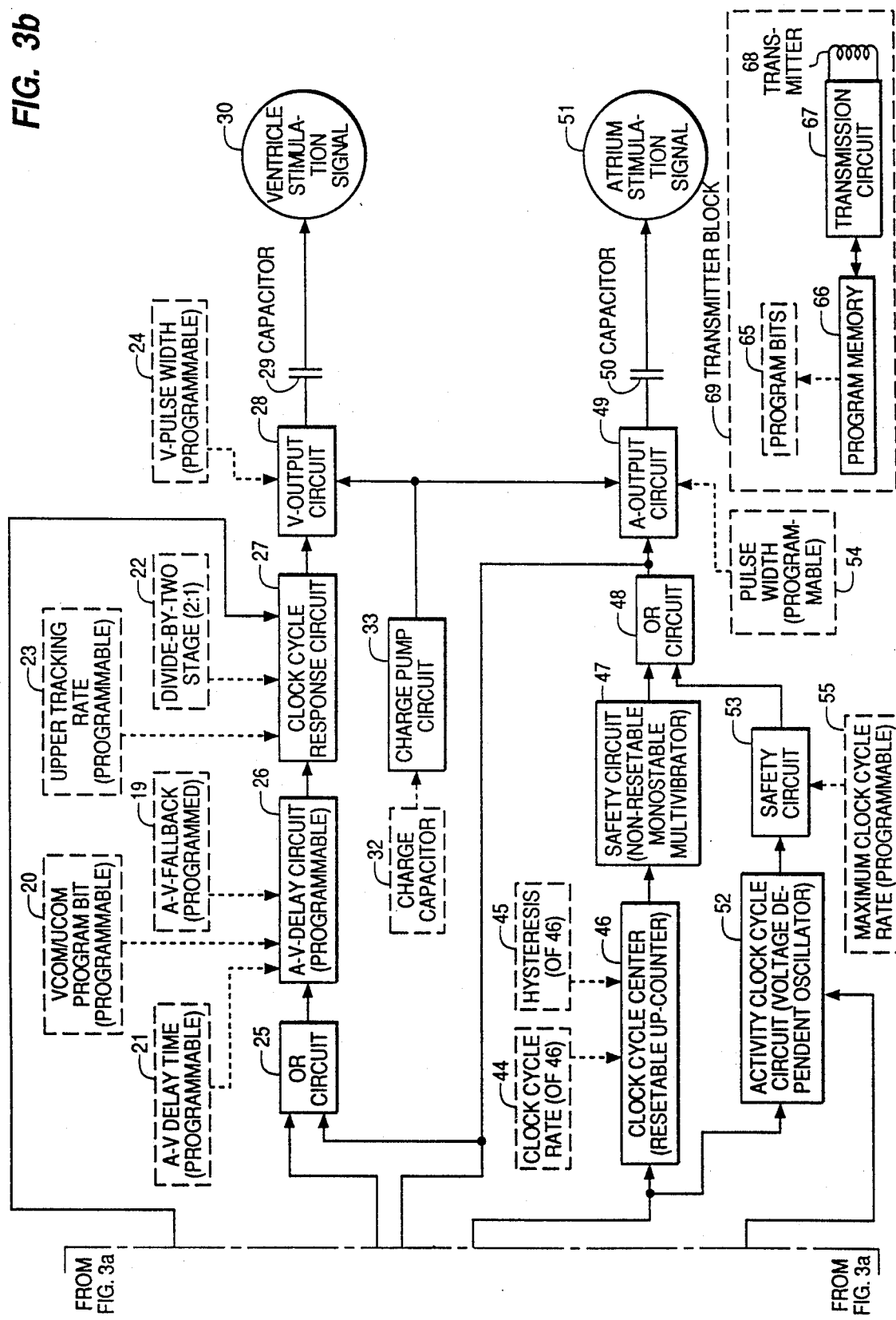

FIG. 3 shows a block circuit diagram of the signal processing circuit whereby the two-chamber pacemaker works in the DDD-mode, i.e. the physiological stimulation of the atrium is included in a cyclic control process. Both of the input channels for the ventricle and the atrium are constructed in a similar fashion. The ventricle detection signal 10 is applied to a V-gating circuit 12 via a capacitor 11 in order to supress the d.c voltage. This gating circuit 12 gates the V-input signal during an output impulse and discharges the capacitor 11 after the output impulse. The output signal of the gating circuit 12 is applied to a V-signal amplifier 14 whose amplification factor is variable and has a bandpass characteristic with a centre frequency of 50 Hz. The V-sensitivity 13 can be programmed externally. The output of the V-signal amplifier 14 is applied to a V-detector 15. This V-detector 15 can be a bipolar peak value rectifier with a fixed detection threshold. The amplification of the V-signal amplifier 14 is set in such a way that the corresponding input signal can be detected.

The digital output signal of the V-detector 15 is applied to a V-signal interference voltage limiter 16. Input signals with a period smaller than 125 ms are gated. The V-signal interference voltage limiter 16 also comprises a gating of the digital signal during an output impulse. For this, the V-signal interference voltage limiter 16 is connected to an input clock cycle circuit 31. The output signal of the V-signal interference voltage limiter 16 is applied to a V-refraction time 18 with a programmable refraction time 17. The V-refraction time circuit 18 cannot be reset. After an input signal is detected for the programmed refraction time no further input signals are thus detected by the circuit. The output signal of the refraction time circuit 18 is applied to a clock cycle response circuit 27.

The atrium detection signal 34 is applied via an A-gating circuit 36 via a capacitor 35 in order to supress the d.c voltage. The output signal of the A-gating circuit 36 is applied to an A-signal amplifier 37 whose amplification factor 38 is variable and has a band-pass characteristic with a centre frequency of 100 Hz. The output of the A-signal amplifier 37 is applied to an A-detector 39. The digital output signal of the A-detector 39 is connected to an A-signal interference voltage limiter 40. The A-signal interference voltage limiter 40 is connected to the input clock cycle circuit 31. The output signal of the A-signal interference voltage limiter 40 is applied to an A-refraction time circuit 41 with a programmable refraction time 42. In order to gate the input signals the gating circuits 12, 36 are connected to the input clock cycle circuit 31. The configuration of the A-channel corresponds to that of the V-channel.

A digital impulse is generated as the output signal for both channels after the refraction time circuits and is derived from a detected happening either in the atrium or the ventricle of the heart. Both input channels have the function of checking the input signals that are fed to the circuit by the atrium or ventricle detectors 10, 34 in order to ensure that all of the desired heart happenings are detected whilst all of the interference signals are eliminated.

The output signal of the A-refraction time circuit 41 is applied to an OR circuit 43 and to an OR circuit 25. The output signal of the OR circuit 43 is applied not only to a clock cycle centre 46 but also to an activity clock cycle circuit 52 comprising a voltage-dependent oscillator. The clock cycle centre 46 is a resetable up-counter, whose clock cycle rate 44 and hysteresis 45 are programmable. This up-counter is clocked by a quarz oscillator. This up-counter of the clock cycle centre 46 provides an output signal when the value of the up-counter of the clock cycle centre 46 reaches the decoded value of the programmed clock cycle rate 44. This output signal, which is applied through a safety circuit 47 in order to prevent too high clock cycle rates, is used to reset the up-counter of the clock cycle centre 46 for a new count period. For this, the output signal is applied via an OR circuit 48 to a further input of the OR circuit 43. The safety circuit 47 consists of a non-resetable monostable multivibrator which limits the maximum clock cycle rate of the clock cycle centre 46 to a fixed value if the clock cycle centre operates faultily. This clock cycle centre 46 is therefore free-running and generates an output signal based on the values of the programmed clock cycle rates. In addition to being reset by its own impulse, the up-counter of the clock cycle centre 46 can be reset by the output signal of the atrium input channel. Hysteresis 45 can be programmed in order to prevent that the up-counter of the clock cycle centre 46 does not, over a longer time period, emit an output signal at a clock cycle rate which is higher than the programmed clock cycle rate due to external resetting. In this way the programmed clock cycle rate 44 can be slightly modified depending on whether the last resetting was caused by the up-counter of the clock cycle center 46 or by the atrium input channel.

The output signal of the voltage-dependent oscillator 52, which is succeeded by a safety circuit 53 with a programmable maximum clock cycle rate 55, which limits the clock cycle rate to a clock cycle rate derived from the maximum activity, is also connected to the OR circuit 48. In this way, not only the clock cycle centre 46 but also the voltage dependent oscillator of the activity circuit 52 can be reset by the same signals.

The clock cycle rate of the voltage-dependent oscillator of the activity circuit 52 is dependent on a signal which is derived from an activity sensor 56 with succeeding threshold detector 57 and signal integrator 58. The threshold value 59 of the threshold detector 57 can be altered by external programming. Attack time 61 and decay time 60 can be programmed for the signal integrator 58. The voltage dependent oscillator 52 can be used to override the clock cycle centre 46 and to increase the output clock cycle up to the maximum programmed activity clock cycle.

The cardiac pacemaker is synchronized with the P-wave or the atrium if the external reset-impulse of the counters 46, 52 is generated by the atrium channel. This type of synchronization exists as long as the atrium channel provides an output clock cycle which is higher than either the programmed clock cycle or the clock cycle derived from the activity. In this case the counters 46, 52 do not emit any output signal and are therefore blocked.

The outputs of the counters 46, 52 are additionally connected to an A-output circuit 49 with a programmable pulse width 54 via the OR circuit 48. The thereby created atrium stimulation signal 51 is applied via a capacitor 50 to stimulate the atrium of the heart. The output of the OR-circuit 25 is connected to a programmable A-V-delay circuit 26. The output signal of the OR circuit 25 which starts the A-V delay circuit 26 represents either a detected atrium event or the output signal of one of the counters 46, 52 which had determined that an atrium event should be initiated. The programmable A-V-delay time 21 represents the time between a synchronized atrium and ventricle event. The A-V-fallback 19 is the programmed difference in the A-V-delay depending on whether the A-V-delay was initiated either by a measured atrium event or by a counter interruption which wants to initiate a clock-cycled atrium event. A programmable $V_{Com}/U_{Com}$ program bit 20 decides whether the cardiac pacemaker is switched over to a ventricular output signal at the end of the A-V-delay if a ventricle event took place within this time.

The output of the A-V-delay 26 is connected to the clock cycle response circuit 27. This output signal is generated in accordance with the programmed A-V-delay time 21. At this point in time the output signal of the ventricle input channel is used to supress a ventricle impulse signal if a ventricle event is detected. If no ventricle event is detected the upper programmable tracking rate 23 is set by the stimulation response. This upper tracking rate is the highest rate at which the successive ventricle output impulses can be passed. The response to this upwardly limited clock cycle rate can also be programmed. For this, either a divide-by-two (2:1) stage 22 or a flat Wenckebach output clock cycle circuit with the highest programmable rate can be used. The output signal of the clock cycle response circuit 27 is applied as an impulse to a V-output circuit 28 with a programmable V-pulse width 24. The thus generated ventricle stimulation signal 30 is applied as a ventricular stimulation through a capacitor 29 to the heart.

The configurations of the A-output circuit 49 and the V-output circuit 28 are similar. The input impulses of these output circuits 28, 49 are used to trigger the negative slope of the output impulse with the programmed pulse width. The amplitudes of the V- or A-output impulses are dependent on the voltage of a charge capacitor 32 of a charge-pump circuit 33. This voltage can be programmed and can be simultaneously programmed for both output circuits 28, 49.

The activity sensor 56, the threshold detector 57 and the signal integrator 58 make up the activity switching circuit which generates a control signal for the voltage dependent oscillator 52. The activity sensor 56 is a piezoelectric element which is preferably attached to the inside of the pacemaker housing. A voltage is generated as the output signal of the sensor 56 which is proportional to the deflection which is caused by body movements and thrusts. The output signal is applied to the threshold detector 57 which comprises a threshold which can be programmed and which gates the signals of the sensor 56 below that threshold. The signal values, which are detected above the activity threshold, are amplified and integrated by the signal integrator 58. The integrated voltage is used to regulate the voltage-dependent oscillator of the activity clock cycle circuit 52. The value of the stimulation rate, up to which the voltage can increase, is the result of the increasing input signal and is called attack and can be programmed.

The value of the stimulation rate, down to which the voltage can decrease, is called decay and can also be programmed. The control quantity 59 is used to alter the effective threshold of the threshold circuit by programming. The control quantities 60 and 61 represent the weighting values which can be programmed for the effect of the times above and below the threshold with regard to the integrator 58. If the integrator is formed, for example by a capacitor, the control quantites influence the charge and discharge current. A middle voltage is formed, which acts as the input voltage for the voltage dependent oscillator 52, if the capacitor is charged in the case of the threshold being exceeded and is discharged if the threshold is not exceeded. If the threshold is exceeded on numerous occassions (high level of activity) the voltage increases and it decreases again if the activity level decreases. The values of the charge and discharge quantities which can be programmed determine the attack and decay constants (see FIGS. 2a and 2b).

In a further advantageous but not-illustrated embodiment, an amplifier, which amplifies the impulses which exceed the threshold—and if neccessary only amplifies them up to the application limitation—is situated between the threshold stage 57 and the integrator 58. In this way the influence of the different classes of impulse amplitude can further influence the basic pacing rate of the cardiac pacemaker due to the non-linear distortion of the amplifier. The rapid alternation between charging when the threshold is exceeded and discharging when the threshold is not exceeded does not noticeably influence the stimulation rate if the value (capacity) of the integrator is appropriately chosen. The change only takes place after a greater number of cycles exceed or do not exceed the threshold.

A supervision circuit 62 of supervisory black 64 checks the capacity of the battery and generates an EOL-signal (end of life), as soon as the capacity falls below a certain value. This signal is used to switch the pacemaker into an EOL-operational mode. That means that the activity switching circuit is switched off and the divider circuit of the quartz oscillator 63 is modified so that all clock cycle circuits run approx. 11% slower.

In transmitter black 69, program memory 66 stores the program bits 65, which monitor the different parameters of the pacemaker. A transmission circuit 67 with connected transmitter 68 consists of a bidirectional communication circuit and is used if demanded, for the external transmission of the momentarily stored data and to take over external modifications in the memory 66.

I claim:
1. A cardiac pacemaker comprising activity sensor means for detecting physical activity of a patient and generating a momentary output signal;

activity clock cycle generator means, having an adjustable clock cycle rate which is adjustable to the activity of the patient, for generating stimulation impulses for cardiac muscles of the patient at a rate defined by an end of one of a basic rate interval and an escape interval, the basic rate interval being a normal interval between stimulating impulses, and the escape interval being an on-demand interval between stimulating impulses; and varying means for varying the basic rate interval and escape interval of the activity clock cycle generator means between upper and lower fixed limits dependent on the activity of the patient detected by the activity sensor means, wherein the varying means includes evaluation means for generating a control signal for controlling the activity clock cycle generator means as a time measurement for the rate of the stimulation impulses based on a comparison of the momentary output of the activity sensor means with a threshold value, wherein the rate of the stimulation impulses is thereby determined by the evaluation means based on a relationship between a time the momentary output signal of the activity sensor means remains above the threshold value and a time the momentary output signal of the activity sensor means remains below the threshold value.

2. A cardiac pacemaker according to claim 1, wherein the relationship between the time the momentary output signal of the activity sensor means remains above the threshold value and the time the momentary output signal of the activity sensor means remains below the threshold value is subjected to weighted averaging by the evaluation means using respective weighting factors for the time the momentary output signal of the activity sensor means remains above and below the threshold value.

3. A cardiac pacemaker according to claim 2, wherein the respective weighting factors for the tim the momentary output signal of the activity sensor means remains above and below the threshold value differ from one another.

4. A cardiac pacemaker according to claim 3, wherein the varying means, including the evaluation means, is programmable, and wherein the respective weighting factors are quantities which can be programmably changed and which define an attack rate and a decay rate of the control signal generated by the evaluation means.

5. A cardiac pacemaker according to claim 4, wherein the momentary output signal of the activity sensor is band-limited by band-limiting means and wherein the control signal generated by the evaluation means is defined by the evaluation means as a mean value of the band-limited momentary output signal of the activity sensor during the time the band-limited momentary output signal remains above the threshold value.

6. A cardiac pacemaker according to claim 5, wherein the evaluation means includes an integrator, the band-limiting means includes a threshold detector, the weighted averaging being carried out by the integrator.

7. A cardiac pacemaker according to claim 6, wherein the integrator consists of a capacitor which is charged and discharged during times, defined by the times the momentary output signal of the activity sensor means remains above and below the threshold value, by current source means having a plurality of predefined programmable current values.

8. A cardiac pacemaker according to claim 6, wherein the band pass filter of said band-limiting means passes a frequency range of 2 to 8 Hz therethrough.

9. A cardiac pacemaker according to claim 4, wherein the attack rate is greater than the decay rate, the values of the attack and decay rates of the control signal coinciding with physiological values of actual physical activities.

10. In a cardiac pacemaker which includes an activity sensor for detecting patient activity and producing momentary output signals, and mans for adapting cardiac stimulation signals to a patient's activity based on the number of momentary output signals received from the activity sensor, an evaluation circuit arrangement for controlling the means for adapting cardiac stimulation signals to patient activity so that activity sensor momentary output signal intensity is taken into account, the arrangement comprising:

threshold detection means, operatively coupled to the activity sensor, for gating the momentary output signals from the activity sensor so that signals below a programmable threshold intensity value are blocked and signals above the programmable threshold intensity value are passed; and signal integrator and amplifier means, operatively coupled to receive signals passed by the threshold detection means, for integrating and amplifying the passed and received signals, and producing an output signal for controlling the means for adapting cardiac stimulation signals to patient activity.

11. The evaluation circuit arrangement according to claim 10, wherein the threshold detection means includes means for setting the programmable threshold intensity value, and wherein the signal integrator and amplifier means comprises a capacitor for integrating the passed and received signals, the signal integrator and amplifier means further comprising programmable attack means for adjusting an attack value corresponding to a charging rate of the capacitor, and programmable decay means for adjusting a decay value corresponding to a discharging rate of the capacitor.

* * * * *